United States Patent [19]

Shinskey

[11] 4,358,346

[45] Nov. 9, 1982

[54] CONTROL OF ALCOHOL DISTILLATION

[75] Inventor: Francis G. Shinskey, Foxboro, Mass.

[73] Assignee: The Foxboro Company, Foxboro, Mass.

[21] Appl. No.: 260,954

[22] Filed: May 6, 1981

[51] Int. Cl.³ .................. B01D 3/42; C07C 29/82
[52] U.S. Cl. ........................................ 203/1; 203/2;
    203/3; 203/19; 203/70; 203/81; 203/DIG. 13;
    202/160; 202/206
[58] Field of Search ............... 203/19, DIG. 13, 1-3,
    203/70, 74-77, 81-83, 96, 97, 91-93; 202/160,
    206; 196/132; 426/494; 364/501; 568/916;
    435/161

[56] References Cited

U.S. PATENT DOCUMENTS

| | | | |
|---|---|---|---|
| 1,469,447 | 10/1923 | Schneible | 203/19 |
| 1,670,053 | 5/1928 | Steffens | 203/19 |
| 1,860,554 | 5/1932 | Ricard et al. | 203/19 |
| 2,199,982 | 5/1940 | Bright et al. | 203/3 |
| 2,684,326 | 7/1954 | Boyd | 203/2 |
| 2,994,643 | 8/1961 | Smalling | 203/3 |
| 3,575,818 | 4/1971 | West | 203/19 |
| 4,168,209 | 9/1979 | Mikitenko et al. | 203/2 |

FOREIGN PATENT DOCUMENTS

| | | | |
|---|---|---|---|
| 628939 | 10/1978 | U.S.S.R. | 203/DIG. 13 |
| 629230 | 10/1978 | U.S.S.R. | 203/DIG. 13 |
| 637427 | 12/1978 | U.S.S.R. | 203/DIG. 13 |
| 639930 | 2/1979 | U.S.S.R. | 203/DIG. 13 |
| 703112 | 12/1979 | U.S.S.R. | 203/DIG. 13 |
| 734265 | 5/1980 | U.S.S.R. | 203/DIG. 13 |

Primary Examiner—Wilbur L. Bascomb, Jr.
Attorney, Agent, or Firm—Andrew T. Karnakis

[57] ABSTRACT

Control of multiple distillation columns for producing anhydrous alcohol suitable for blending with gasoline to produce gasohol. The distillation process involves production of a first-stage distillate containing a predetermined amount of water, followed by azeotropic distillation in the presence of a hydrocarbon entrainer to strip the distillate of its water content, leaving anhydrous alcohol as a bottom product. Tight controls are present during first-stage distillate production to hold its proof at an optimum value derived at through material balance calculations to minimize energy consumption for the overall system. Control over the dehydrating stage is accomplished by a combination of ratio control to regulate and maintain the proper proportion of the entrainer and temperature control to regulate within the column the actual inventory of entrainer. This latter control loop includes adjusting the rate of boiling so as to be sufficient to keep the hydrocarbon out of the alcohol product and yet not high enough to drive alcohol overhead out of the column.

10 Claims, 2 Drawing Figures

CONTROL OF ALCOHOL DISTILLATION

FIELD OF THE INVENTION

This invention relates to the control of distillation columns in general, and particularly to the control of such columns for producing anhydrous alcohol, especially pure ethanol suitable for blending with motor fuel.

BACKGROUND OF THE INVENTION

The commercial production of alcohol by distillation has been in widespread operation for many years. Control systems for assuring product quality within reasonable efficiency limits have paralleled the growth of this industry. In the past, most of the alcohol distilled was for beverage purposes, and accordingly, there was no crucial requirement for a dehydrated end product, thereby alleviating to some extent both the energy required to distill the alcohol and the need for tight controls over the process. However, the rising cost of energy has focused attention on the need for better product optimization of energy intensive (endothermic) processes such as distillation through the application of dynamic control strategies.

Attempts to alleviate energy dependence on petroleum based fuels have been directed to the use of renewable energy source. One such technique involves the production of ethanol from grain for blending with gasoline to form the motor fuel "gasohol". To be effective as an alternative energy source, the process by which the ethanol is produced must minimize energy consumption so as to achieve "a net energy gain," and moreover final stage ethanol should be essentially anhydrous.

The net effect of these circumstances is to place an increased emphasis on the systems controlling the operation of the distillation unit so that the desired end products can be produced with minimum energy drain. In the specific example of pure ethanol production, the problems are compouned because, as is well known, ethanol and water form an azeotrope whose water percentage is unacceptable for use in making gasohol. To separate the components of the azeotrope, further process steps over and above conventional distillation are required involving the expenditure of more energy and rather expensive entrainer substances. All of this adds detrimentally to the overall cost of making the finished product to desired specifications.

Although a variety of techniques have been applied in the past for the control of alcohol distillation columns, these methods usually rely on simple temperature measurements in conjunction with single-loop flow and level controllers. Generally these loops respond to conditions occurring external of the columns which are used to predict internal column activity; however, such control loops are slow responding and, most often, not truly representative of the dynamics within the column. Such techniques have thus had difficulties in maintaining effective control over the process, most notably during upset process conditions. This results in particularly significant deficiencies in bringing about unacceptable alcohol losses, high energy consumption, contaminated end product or combinations of the above. Therefore, at present there is a pressing need for an improved process for controlling the production of anhydrous alcohol through a multi-stage process involving a combination of conventional distillation and azeotropic distillation.

SUMMARY OF THE INVENTION

The present invention is directed to the control of multiple distillation columns for the production of anhydrous alcohol. The control system is readily implemented with either pneumatic or electronic instrumentation and provides a dehydrated, uncontaminated end product with minimal overall energy consumption and minimal loss of alcohol.

In a preferred embodiment of the invention to be described below, production of anhydrous ethanol from grain is accomplished in three stages, the first involving stripping the alcohol from the solid grain, the second including passing the just derived alcohol vapor to a conventional distillation rectifying column to produce a distillate of predetermined product proof, with the third stage being a dehydrating column (dehydrator). This final column involves introduction under controlled conditions of an azeotropic entrainer, such as pentane—a volatile hydrocarbon. As is known, it is highly desirous to precisely match the proper molecular proportions of entrainer to the amount of water entering the dehydrator.

Control over the stripping and rectifying stages of the process is achieved by proper regulation of steam supplied to the first stage column (beer still) which drives alcohol vapor overhead and leaves solids and water at the bottom of the column. Rectifying column control is more or less conventional, but the proof of the distillate is closely regulated because, as will be explained in detail subsequently, product proof at this stage is an important parameter in minimizing energy consumption.

Control over the dehydrating stage is accomplished by a combination of ratio control to regulate and maintain the proper proportion of the entrainer and temperature control to regulate within the column the actual inventory of entrainer. This latter control loop includes adjusting the rate of boiling so as to be sufficient to keep the hydrocarbon out of the alcohol product and yet not high enough to drive alcohol overhead out of the column.

Considering the control system with more particularity, near the top of the rectifying column vapor pressure is compared to that of azeotropic alcohol at about 190 proof. Although feasible to produce at this stage in the process a drier product, the effect of having a greater amount of water entering the dehydrator is predetermined such that the boilup rates of the beer still and dehydrator combined are lower than would have resulted from the dehydrator having to accommodate a higher proof feed. Thus an important part of the overall control of the azeotropic production and dehydration stages involves considering the two in concert so that the overall energy consumption for the system is minimized.

Within the dehydrator, the control system is constructed so as to maintain the dynamic inventory of hydrocarbon entrainer in the top part of the column. This is accomplished by sensing the temperature near the top and the middle of the column. A large differential temperature indicates insufficient hydrocarbon in this region and results in the generation of a control signal which raises the amount of entrainer entering as reflux. A differential-vapor-pressure sensor at the bottom of the column detects excess hydrocarbon and through a controller increases the rate of boilup to the column driving the hydrocarbon upward.

By performing material balance calculations for each column of a given production plant, the optimum proof of alcohol that is supplied to the dehydrating column can be found and controllers adjusted accordingly to minimize energy consumption of the distillation system as a whole.

Other aspects and advantages of the present invention will become apparent in light of the following description read in conjunction with the associated drawings.

DESCRIPTION OF THE PREFERRED EMBODIMENT

Process Overview

Figures 1, 1A:
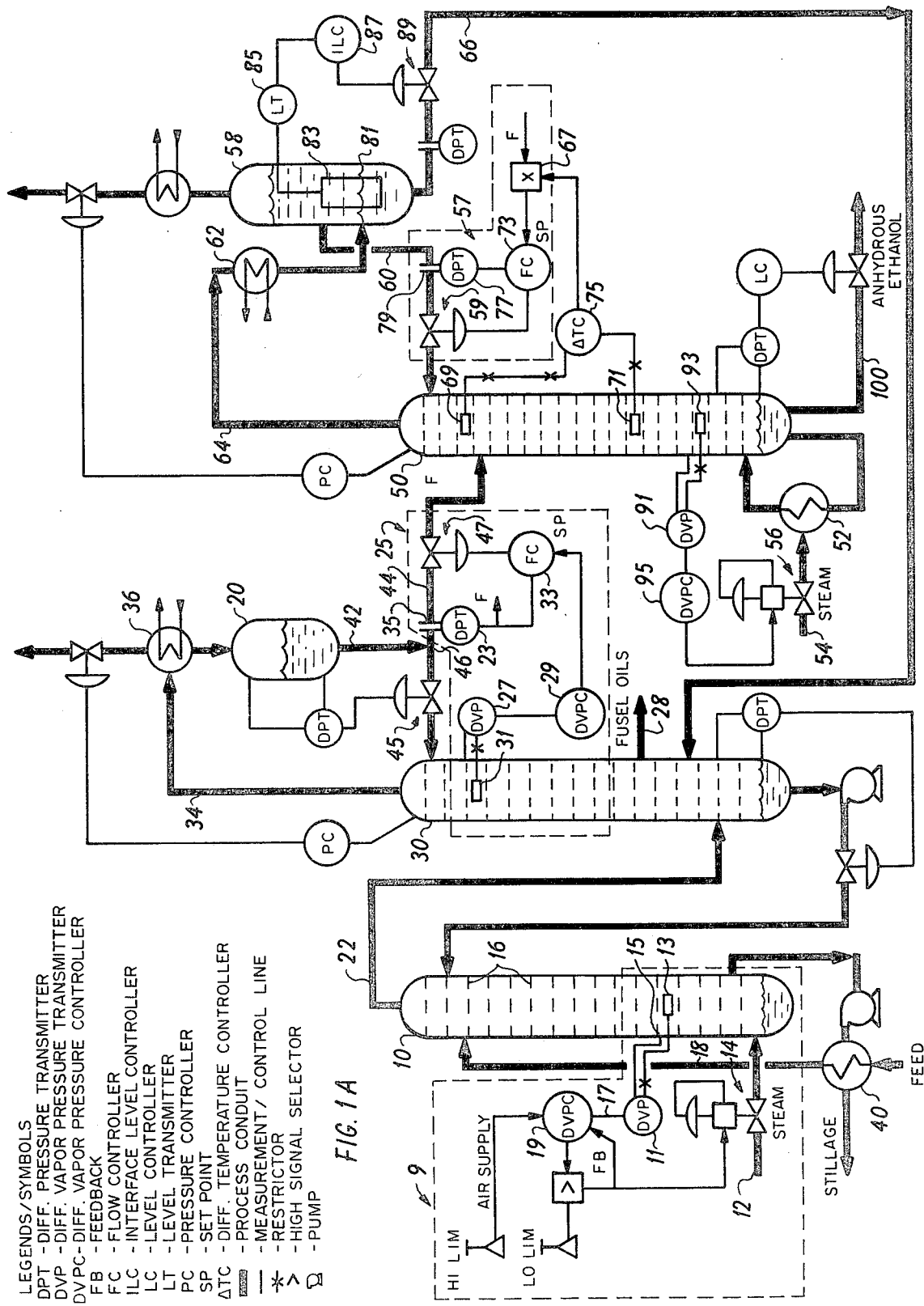
FIG. 1 is a schematic diagram of an anhydrous ethanol production plant with its associated controls.
FIG. 1A is a chart depicting the definition of the symbols and nomenclature found in FIG. 1.

FIG. 1 is a schematic diagram of an azeotropic distillation process plant for the production of anhydrous alcohol from fermented grain, otherwise known as beer. For ease in explanation, the plant as shown is divided into three major areas, each with its own column, namely, a beer still 10 where solid mash is stripped of its alcohol; a rectifying column 30 for producing azeotropic alcohol of 190 proof; and a dehydrating column (dehydrator) 50 from which anhydrous ethanol (200 proof) is separated as a bottom product. In actuality, the rectifying column is placed in close thermal proximity, most often on top of the beer still, to enhance the heat transfer characteristics involved in both stripping alcohol from the beer and volatilizing the remaining liquid to produce the desired proof azeotrope. There is a feed preheater-heat exchanger 40 associated with the beer still. It is reboiled with open steam, whereas the dehydrator has a separate reboiler 52. The columns are heated via steam lines 12, 54. Regulation of heat energy supplied is accomplished by appropriate manipulation of individual steam valves 14, 56 respectively located in the lines 12, 54.

The remainder of the process plant (aside from the arrangement of the control system) includes conventional apparatus such as pumps, condensers, accumulators, valves, and the like whose operation and use is well understood by those of skill in the art. Specific comments concerning various functional details of such items as they relate to the overall control strategy will be deferred until later. For enhanced representation, a graphic distinction is made between the conduits for transferring product from one column to another (indicated by the double-thick lines) and the measurement and control lines (shown with narrow width lines). The various symbols and nomenclature used on the drawing are conventional and well known to those in the art, but nevertheless are included in the chart of FIG. 1A.

Turning now to an overview description of the process, the feed entering the beer still 10 is, as previously noted, a mixture of fermented grain containing about 10 percent ethanol. The beer is preheated in the heat exchanger 40 against stripped stillage (i.e., the bottom product) before being transported to the top of the still by a conduit 18. The construction of sieve trays 16 for such a still is well known to those skilled in the art, primarily involving perforations sufficiently large so as not to plug with grain. However, as will be explained, this construction limits to a narrow range the amount of permissible vapor flow. Steam is introduced at the bottom of the column to boil the beer still through the valve 14.

After sufficient heating, a mixture of ethanol and water vapor richer than 10 percent ethanol by weight is carried out of the top of the beer still 10 to the bottom of the rectifying column 30 by means of a conduit 22. The rectifying column is similarly of conventional structure with the low-ethanol content vapor traveling upward in contact with a downward flow of liquid from an accumulator 20 that refluxes the beer still. The effect of this distillation is to produce an ethanol-rich vapor at the top of the column.

Also occurring during the rectifying stage is a buildup of undesired azeotropes called fusel oils whose boiling point is between ethanol and water. To prevent undesirable accumulation and hence boilover to the overhead product, a conduit 28 near the bottom of the column withdraws periodically or continuously a sidestream from which fusel oil is transported to an accumulator (not shown) for recovery.

The overhead vapors of the desired proof ethanol are passed out of the rectifying column 30 through a conduit 34 to a condenser 36 where they are cooled and collected in the accumulator 20. No phase separation between ethanol and water occurs in this condensed state. The liquid in the accumulator is withdrawn by a conduit 42 where it intersects a main conduit 44 linking the rectifier 30 and the dehydrator 50 at a "T" branch 46. Here, depending on the positioning of a pair of control valves 45, 47, part of the ethanol-water mixture is returned to the rectifier as reflux and the remainder is fed to the dehydrator along the conduit 44.

Within the dehydrator 50, a predetermined amount of entrainer initially stored within an accumulator 58 is introduced as reflux through a control valve 59 by means of a conduit 60. This forms a ternary azeotrope whose boiling point is below ethanol and which contains a water-to-ethanol ratio higher than the feed, thereby resulting in the preferential distillation of water (together with entrainer) overhead, with anhydrous ethanol left as bottom product. After passing through a condenser 62 connected by a conduit 64 to the top of the dehydrator, the subcooled liquid separates into two layers within the accumulator 58. The light, top layer, of predominantly entrainer is returned as reflux via the conduit 60, whereas the heavy, bottom layer of predominantly ethanol and water is recycled along a conduit 66 to the rectifying column 30.

Control Systems

An inspection of FIG. 1 immediately highlights the control instrumentation used in the production process, with the thin-lined measurement and control signal paths emanating from and/or terminating at the circled representations of the various portions of the instrumentation package. The larger circles whose identifiers end with the letter "C" depict controllers, while the smaller circles represent transmitters. At this point it may be helpful to review the definitions found in FIG. 1A. It should be noted that the control system for this installation is implemented with pneumatic transmitting instruments and controllers of the type readily commercially available from a variety of manufacturers, as, for example, The Foxboro Company, as listed in its General Catalog #577. However, the nature of the control instrumentation is irrelevant to the working of the present invention, as it may just as easily be implemented with analog or digital electronic controls.

The primary control over the beer still 10 rests with the amount of steam supplied to boil the beer resulting from a control loop 9 contained within the dashed lines. To assure that sufficient steam is being added to strip the ethanol from the grain to thus keep the ethanol out of the bottom, a differential-vapor-pressure transmitter 11 with a water-filled temperature bulb 13 is placed near the bottom of the still. Such transmitters are often used in distillation control and are commercially available from The Foxboro Company as Model No. 13VA. This unit is essentially a differential-pressure measuring device whose low-pressure measurement is attached to a temperature bulb filled with a sealed reference fluid of known composition containing the substance and its vapor, about which control is to be effectuated. A high pressure connection indicated at point 15 is maintained at the same elevation as the bulb 13, thus allowing a proportional pressure difference to be transmitted along a control line 17 to a differential-vapor-pressure controller 19 whose set point is maintained slightly above zero differential vapor pressure. Hence, in this specific instance, if alcohol being drifting down the column, the vapor pressure at that point in the column will exceed that of the water in the bulb, a signal will be sent to the differential-vapor-pressure controller producing an error signal which results in the controller generating an output signal to appropriately increase the level of steam entering the column.

As shown, high and low limits are set into the differential-vapor-pressure controller 19 to regulate the maximum and minimum amount of steam which can flow through the steam valve 14 into the still. Such limits would, of course, vary according to the internal structure of the particular still. However, generally such limits are required to prevent too much steam flow which would result in solids being carried up and out into the rectifying column 30. On the other hand, if too little steam is supplied, this would result in too little a vapor flow along the trays causing the feed to weep through the perforations. The concomitant reduction in liquid level on the trays would allow ethanol to drop to the bottom and escape unrecovered with the stillage. In either event, once the internal design of the still is known, the desired limits can be set by observing the pressure drop across the trays.

After the ethanol-enriched vapor enters the bottom of the rectifying column 30, it encounters a downward flow of reflux of condensed ethanol/water vapor stored in the accumulator 20 after having been withdrawn from the top of the column 30. Reflux is controlled by the level of liquid in the accumulator 20 as determined by a differential pressure transmitter 23 which regulates the positioning of the control valve 45 to adjust the amount of reflux required in relation to the withdrawn product. Meanwhile the concentration of ethanol in relation to the amount of water in the vapor withdrawn is controlled by the rate of its withdrawal. The controls required are included within the dashed lines as signified by the reference numeral 25. The composition being withdrawn is sensed by a second differential-vapor-pressure transmitter 27 and its associated controller 29. It is possible to approach an azeotropic composition of 95.6 percent ethanol by weight but is more practical to produce at this stage 90 percent ethanol as sufficient water will be necessary to form a separate phase in the accumulator 58 of the dehydrating column 50. This desired proof is controlled by having the temperature bulb 31 of the differential-vapor-pressure transmitter 27 filled with 95 percent ethanol. The exact concentration of ethanol in the bulb is not crucial, because vapor pressure in the range of 95 to 100 percent is fairly constant.

If the amount of ethanol is being withdrawn too rapidly, this will be sensed by a decrease in vapor pressure at the top of the column. The corresponding controller output signal is cascaded as the set-point input to a flow-indicating controller 33 whose measurement input is derived from the combination of the differential pressure transmitter 23 and an orifice plate 35. The output of the flow indicating controller closes the control valve 47 to reduce the amount of withdrawal. Just the opposite effects and corresponding actions occur if too little ethanol is withdrawn.

The setpoint of the differential-vapor-pressure controller 29, which is the desired proof of the ethanol-water mixture, is chosen to take into account the energy consumption needs of the beer still and that of the dehydrator. Although allowing more water to be contained in the overhead vapor at this point requires more steam in the dehydrating stage, concurrently less steam will be required in the beer still. The optimum point may be chosen for each individual process plant, bearing in mind the number of trays in the particular column, their efficiency and the type of hydrocarbon entrainer utilized.

Although simultaneous control of product composition at remote ends of a distillation column (in this case the stripping of alcohol from beer at the bottom of the beer still 10 by control of heat input and the production of relatively impure ethanol at the top of the rectifier 30 by control of withdrawal rate) does result in a degree of interaction between the two control loops, it is possible using the procedures outlined by Shinskey in his book entitled "Distillation Control for Productivity and Energy Conservation" to predict the severity of the interaction. In the embodiment being described, the relative gain between the two loops was calculated to be in the range of 0.9 to 1.0. Relative gains approaching unity indicate very little interaction is present between the two loops. In fact, the control of ethanol content in the top product may be controlled to any desired concentration over a wide operating range.

The feed is admitted near the top of the dehydrator column by the conduit 44. A signal representing this feed rate, indicated schematically by the letter "F," is shown entering a multiplier unit 67 whose operation will be more fully explained presently. Azeotropic distillation by addition of pentane or other suitable hydrocarbon as an entrainer has been the subject of recent study. For example, a paper by C. Black, entitled, "Distillation Modeling of Ethanol Recovery and Dehydration Process for Ethanol and Gasohol" in the September 1980 issue of Chemical Engineering Progress discusses in detail how to calculate the amount of hydrocarbon required to effectuate separation. According to Black, for an incoming feed to a stripper column (i.e., dehydrator) containing about 7.5% water and utilizing a pentane entrainer, a nineteen-tray dehydrator would produce the desired separation if an entrainer-to-ethanol ratio of approximately 3.0 (mole basis) or 4.69 (mass basis) were maintained. To assure success in the event of upset conditions, past control strategies involving azeotropic distillation have been geared around adding excess amount of hydrocarbon as reflux to bring about the desired separation. However, even this is uncertain during periods of upset, and as previously mentioned above, energy inefficient, as all the entrainer must be heated to the boiling point and vaporized.

Figure 2:
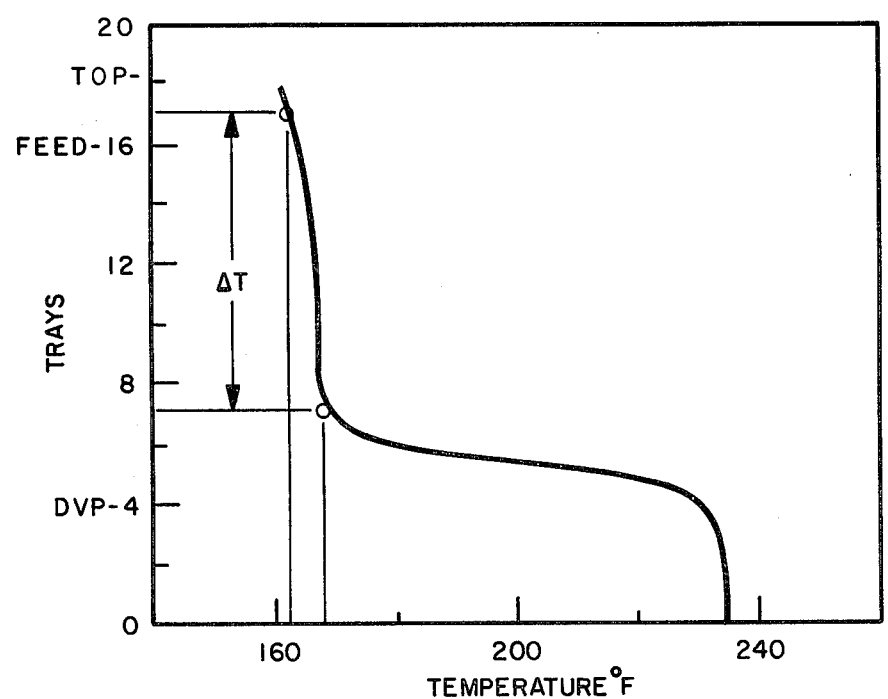
FIG. 2 is a graph of the temperature profile for a 20-tray azeotropic dehydrating column, using n-pentane entrainer.

An important aspect of the control system of the present invention is that the amount of entrainer introduced as reflux in the dehydrator column 50 is adjusted depending on the concentration of hydrocarbon (e.g., pentane) within the column itself. At initial conditions, with all compositions assumed constant, the reflux-to-feed ratio needed for water removal is set as calculated according to the water content of the feed. This is accomplished by introducing the feed flow signal into the multiplier unit 67. However, such a setting is approximate being contingent on accuracies of flowmeters and constant compositions. To bring about the desired "on-line" control, a feedback loop centered around a pair of temperature bulbs 69, 71 located respectively near the top and at mid-column point of the dehydrator 50 is added. Composition profiles, as indicated in the above-mentioned Black article, have shown that the concentration of pentane, and therefore column temperature, varies little from the top of the column to past the mid-column point (see FIG. 2). Hence, any significant temperature difference sensed by the bulbs 69, 71 will cause a differential-temperature controller 75 to send an appropriate feedback signal to the multiplier unit to increase the rate of reflux from the accumulator 58. This is done by a reflux flow loop 57 consisting of a flow indicating controller 73 receiving inputs from both the multiplier unit and a differential pressure transmitter 77 in concert with an orifice plate 79. The output of the controller 73 manipulates the control valve 59 to adjust the rate of reflux.

Within the accumulator 58, a liquid phase separation occurs between the entrainer (the top layer) and the water-rich ethanol on the bottom as shown by the reference numeral 81. The level of the aqueous layer in the accumulator 58 is controlled by manipulation of its rate of withdrawal, with the interface 81 being sensed by the buoyant force acting on a float 83 suspended therein. The location of the interface is sensed by a level transmitter 85 which acting through an associated controller 87 regulates the amount of water/ethanol mixture withdrawn through a control valve 89 by the conduit 66 for recycling in the rectifying column 30. The present arrangement can thus be seen to include enough water in the feed to produce a phase separation in the accumulator 58 relatively soon after startup, but to prohibit excess buildup of the aqueous layer to prevent overfill and subsequent flooding of the dehydrator. Although not specifically controlled, the level of entrainer is free to move as its inventory shifts between the dehydrator column and the accumulator. Therefore, periodic losses of hydrocarbon solvent will have to be made up by introduction of new solvent in the decanter.

In order to keep the entrainer out of the bottom product, i.e., the anhydrous alcohol, a third differential-vapor-pressure transmitter 91 is located near the bottom of the column 50. The bulb 93 of this transmitter is filled with pure ethanol, and hence a rising vapor pressure at this position will indicate the presence of entrainer. A signal is then sent to a differential-vapor-pressure controller 95 whose output is in turn fed to the steam valve 56 to adjust the rate of steam passing through the reboiler 52 for entry to the dehydrator column. The effect of this control loop is to drive the entrainer upward. It should be remembered that the differential-vapor-pressure transmitter 91 is insensitive to the presence of water at this level in the column; therefore, two composition control loops are required, with water removal accomplished by manipulation of reflux, as described above.

Anydrous alcohol is withdrawn from the bottom of the dehydrator 50 through a conduit 100 while the water/ethanol mixture, withdrawn as the lower layer from the accumulator 58, can either be recycled into the rectifying column or drawn off as an end product for use in another application.

Although a preferred embodiment has been set forth in detail above, this is solely for the purpose of illustration. Modifications will become apparent to those skilled in the art without departing from the scope of the present invention as defined in the accompanying claims.

What is claimed is:

1. A method for controlling the production of anhydrous alcohol comprising the steps of:

distilling in a first column means a mixture of material containing alcohol to form an azeotrope of water and alcohol;

introducing said azeotrope as a feed to a second column means;

adding a predetermined amount of a hydrocarbon solvent to said second column to permit separation of said azeotrope;

detecting within said second column a change in the concentration of said hydrocarbon solvent;

automatically regulating in response to said detected change the amount of said hydrocarbon solvent within said second column to maintain the proper proportion of solvent to water thereby compensating for variances in the composition of said feed; and regulating the rate of boiling in said second column to separate said azeotrope and to remove said hydrocarbon solvent from the anhydrous alcohol.

2. The method of claim 1 including the step of controlling the proof of said azeotrope formed in said first column means to a predetermined value calculated to minimize the energy consumption of both of said column means.

3. The method of claim 2 wherein said predetermined value is controlled by measuring near the top of said first column means the differential vapor pressure, comparing said vapor pressure to that of an azeotrope of alcohol and water of said predetermined value, and adjusting the rate of withdrawal of said azeotrope from said first column means.

4. The method of claim 1 wherein said hydrocarbon solvent is introduced near the top of said second column means as reflux.

5. The method of claim 4 wherein the amount of said hydrocarbon solvent within said second column means is maintained in the top section thereof.

6. The method of claim 5 including the step of generating a signal representative of the rate of feed of said azeotrope into said second column means for initially setting the reflux-to-feed ratio needed to remove water from said azeotrope.

7. The method of claim 6 including the further step of producing control signals when the concentration of said hydrocarbon solvent deviates from a predetermined control value to appropriately regulate the reflux-to-feed ratio.

8. The method of claim 7 wherein the concentration of said hydrocarbon solvent is detected by temperature bulbs positioned near the top and midpoint respectively of said second column means.

9. The method of claim 8 including the step of sensing the presence of said hydrocarbon solvent approaching the bottom section of said second column means to adjust the rate of boiling accordingly to drive said hydrocarbon solvent upward.

10. The method of claim 1 wherein said material containing alcohol is fermented grain.

* * * * *